US00PP28774P3

(12) United States Plant Patent
Maillard et al.

(10) Patent No.: US PP28,774 P3
(45) Date of Patent: Dec. 19, 2017

(54) PEACH TREE NAMED 'CRISPONDA'

(50) Latin Name: ***Prunus persica* (L.) Batsch**
Varietal Denomination: CRISPONDA

(71) Applicant: AGRO SELECTIONS FRUITS, Elne (FR)

(72) Inventors: Arsène Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 96 days.

(21) Appl. No.: 14/757,157

(22) Filed: Nov. 27, 2015

(65) Prior Publication Data

US 2016/0165775 P1 Jun. 9, 2016

(30) Foreign Application Priority Data

Nov. 27, 2014 (QZ) ..... PBR 2014/3169

(51) Int. Cl.
*A01H 5/08* (2006.01)

(52) U.S. Cl.
USPC ..... Plt./197

(58) Field of Classification Search
USPC ..... Plt./197
See application file for complete search history.

*Primary Examiner* — Anne Grunberg
(74) *Attorney, Agent, or Firm* — Westerman, Hattori, Daniels & Adrian, LLP

(57) ABSTRACT

A new and distinct variety of yellow peach tree denominated 'CRISPONDA' has fruits with high eating quality and very long shelf life without alteration before and after harvesting, with a semi-sweet orange yellow flesh, with a pink red pigmentation near the pistil cavity, and an attractive luminous skin with a high percentage of purple red blush on skin surface. This variety is suited for low chill areas.

2 Drawing Sheets

Botanical classification: *Prunus persica* (L.) Batsch.

Variety denomination: 'CRISPONDA'.

This application claims priority of Community plant variety right No. 2014/3169 filed on Nov. 27, 2014 (Nov. 27, 2014) which is hereby incorporated by reference in its entirety.

BACKGROUND OF THE NEW VARIETY

The present invention relates to a new and distinct variety of yellow peach tree, *Prunus persica* (L.) Batsch, which has been given the variety denomination 'CRISPONDA'. This new tree produces fruits with a long shelf life without alteration both on the tree after growth completion and after harvesting, very good eating quality, clingstone orange yellow flesh fruits for fresh market in July in the Pyrénées-Orienteles department, France. Contrast is made to 'CRISPRIM' yellow peach tree (non patented), for reliable description. 'CRISPONDA' is a promising candidate for commercial success in that it has very attractive fruits with very long shelf life without alteration both before and after harvesting.

ORIGIN OF THE VARIETY

The 'CRISPONDA' yellow peach tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'CRISPONDA' variety resulted from a pollinated cross between the 'NECTABELLE' (U.S. Plant Pat. No. 21,140) yellow nectarine tree, which was used as the seed parent, and the unselected cultivar "ASF I0104" (non patented) yellow peach tree which was used as the pollen parent.

The 'CRISPONDA' variety was obtained by hybridizing and propagated by grafting on a "INRA® GF677" rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'CRISPONDA' yellow peach tree blooms during February or early in March near Elne in the Pyrénées-Orientales department, France. More particularly, it blooms between February $2^{nd}$ and March $6^{th}$, before 'CRISPRIM' yellow peach variety (non patented). The blooming period is considered very early to early. However, it was observed that its early date of blooming seems to be highly dependant on climatic conditions.

The first fruit of 'CRISPONDA' ripens generally during June, approximately four days after the first fruit of 'CRISPRIM' yellow peach variety (non patented). More particularly, it usually ripens between June $9^{th}$ and July $1^{st}$. However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Figure 1:
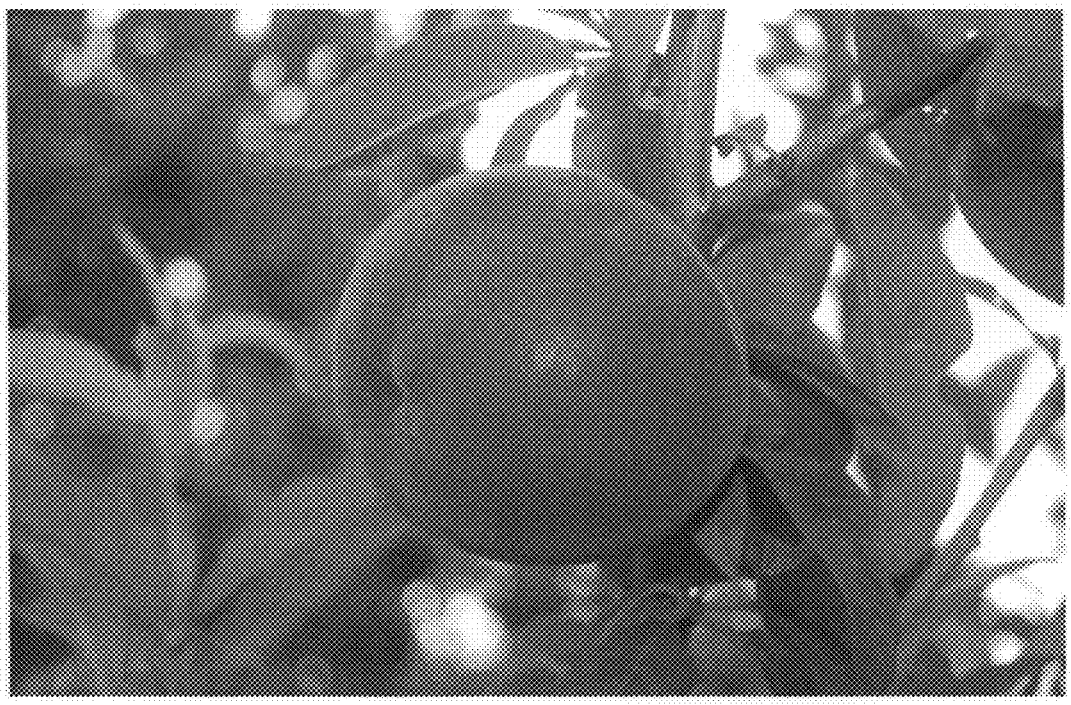
FIG. 1 is a color photograph showing a branch of a tree of the new variety in orchard, bearing fruits.
Figure 2:
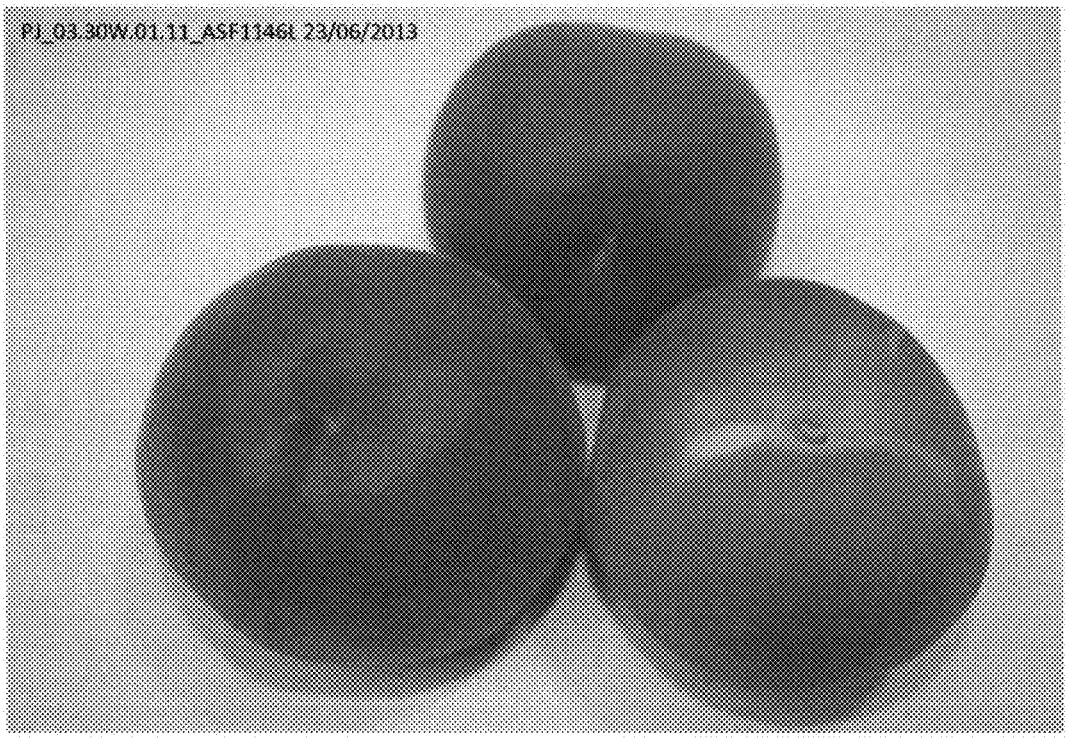
FIG. 2 is a color photograph that shows a different close views of typical fruits of the new variety 'CRISPONDA' at ripening time.
Figure 3:
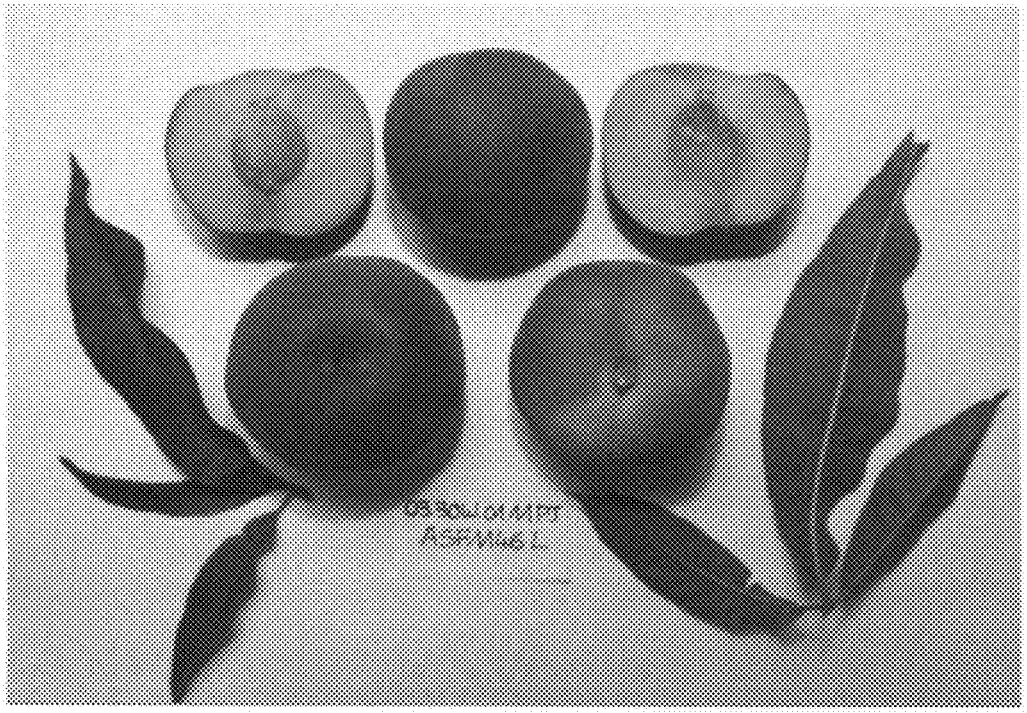
FIG. 3 is a color photograph which shows leaves of the new variety and four typical specimens of the fruit, one having been cut in half with the pit being left into one of the halves for depicting fruit flesh and pit of the new variety.
Figure 4:
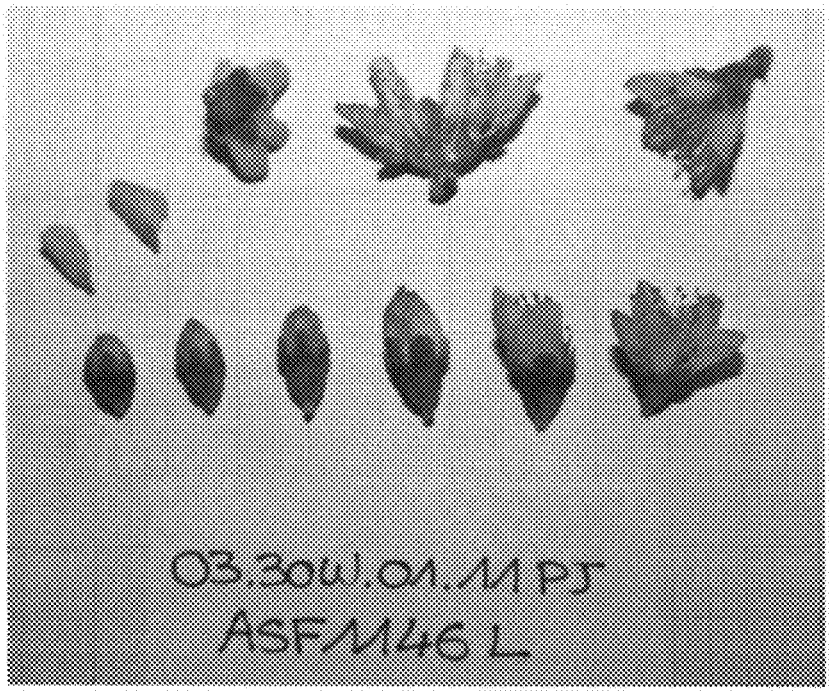
FIG. 4. is a color photograph which depicts the flower buds at different development stages, and the reverse and side view of the flower and the reproductive organs with petals removed, of the new variety.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruits by 'CRISPONDA' is high, due to fruit very long shelf life without alteration after harvesting.

Trees are medium vigorous and large stature half-standing in a semi-flared to semi-upright out aspect. The anthocyanic coloration of flowering shoot is present excluding brushwood side away from sun. The time of beginning of flowering is considered very early to early; flowering begins during February, generally early in February. The type of flower is non showy with small petal size. Petals are dark pink. Leaf glands are present and reniform. The fruit flesh is yellow to orange generally with a pink red pigmentation near the pistil cavity. The fruit skin is very thick, with a luminous purple red blush on a red orange background. The stone is clingstone and his size is considered large. Fruit taste is semi-sweet, very aromatic and with a high level of sugars.

Compared to 'CRISPRIM' (non patented) yellow peach tree, 'CRISPONDA' variety blooms earlier. The blooming period of 'CRISPONDA' variety is considered very early to early whereas the 'CRISPRIM' variety shows a medium blooming period. However, the first fruit 'CRISPONDA' ripens approximately 4 days after the fruits of 'CRISPRIM' variety. Moreover, 'CRISPONDA' fruits are very round to slightly flattened whereas the 'CRISPRIM' variety produces fruits that are round-shaped. The flavour of 'CRISPONDA' fruit flesh is more aromatic than the fruit flesh of 'CRISPRIM'.

Compared to its female parent 'NECTABELLE' (U.S. Plant Pat. No. 21,140), which is a yellow nectarine tree, the new variety 'CRISPONDA' is a yellow peach tree. The two varieties are also different regarding their period of ripeness. Indeed, the fruits of the new variety 'CRISPONDA' ripen between 1 week and 10 days later than the fruits of 'NECTABELLE'. Both varieties have a campanulate-type of flowers (non-showy type). The bloom quantity produced by 'NECTABELLE' variety, i.e. 35 to 40 flowers per meter, is more important than the bloom quantity produced by the new variety 'CRISPONDA', typically between 25 and 30 flowers per meter. The size of the fruits of the new variety 'CRISPONDA' is considered homogenous A-2A and bigger than the size of the fruits of 'NECTABELLE', which are homogenous A in size.

The male parent "ASF I0104" (non patented) of the new variety is a yellow peach tree for which no fruit has been observed nor other characteristics.

DETAILED DESCRIPTION

Referring more specifically to the pomological details of this new and distinct variety of yellow peach tree, the following was observed on trees in their fourth growing season (third year of production) for trees, fruits, leaves and stones and in their third growing season (second year of production) for flowers, under the ecological conditions prevailing at the orchards located near the town of Elne, Pyrénées-Orienteles departement, France. All observations have been done on rootstock cultivars. Used rootstocks were "INRA® GF677" trees. All major color code designations are by reference to The R.H.S. Colour Chart (Fourth Edition) provided by The Royal Horticultural Society of Great Britain.

TREE

Size:

*Generally*.—Considered large. The tree size the first year was approximately 250 cm. The tree was pruned during each following dormant season to a height of approximately 250 cm. Current season shoots growth could reach 60 to 80 cm. The tree size from the second year (second and next years) reached a final height of 310 to 330 cm including current season shoots length. The tree size is consistently reduces to 250 cm the next years.

Spread: Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

Vigor: Considered strong. Probably useful to reduce the supply in nitrogen nutriments in order to avoid an excessive vegetation.

Productivity: Very Productive and regular, every year. Fruit set is spaced by thinning to develop the remaining fruit into the desired market sized fruit. The number of the fruit set varies with the prevailing climatic conditions and cultural practices employed during the bloom period, and is therefore not distinctive of the present variety.

Bearer: Very regular. The fruit distribution is considered homogenous on mixed branches and spurs having more than 1 year. A reduced thinning is performed, regarding the ability of the new variety to produce homogenous fruits having an interesting potential in terms of size.

Form: The 'CRISPONDA' variety has naturally a semi-flared to semi-upright shape.

Density: Considered dense.

Hardiness: The present tree was grown and evaluated in France. The variety appears to be hardy under the central Pyrénées-Orientales departement typical climatic conditions. Experimentations in the same orchard in Elne, Pyrénées-Orienteles department, with winter chilling requirement below 7.2° C. comprised between 350 hours and 1200 hours depending on the specificities of the year, namely, 1076 hours in 2012-2013, 767 hours in 2013-2014, 552 hours in 2014-2015 and 721 hours in 2015-2016, showed a good behaviour of the tree in all cases. No damages were caused by ascertained temperatures as low as −12 degrees Celsius in winter. The tree was also very resistant to frosty springtime weather.

TRUNK

Diameter: Approximately 4.9 to 6.4 centimeters in diameter when measured at a distance of approximately 30 centimeters above the soil level.

Bark texture: Considered slightly rough, with lenticels.

Lenticels: Numerous lenticels are present. The number of lenticels reaches 3 or 4 lenticels per $cm^2$. The lenticels range in size from approximately 3.0 millimeters to 6.0 millimeters in width, and approximately 1.5 millimeters in height.

Lenticel color: The outside of lenticels has a silver-grey color (RHS Grey 201 D), whereas the inside is considered brown (RHS Greyed Orange 165 B).

Bark coloration: The bark has a silver-grey color (RHS Grey 201 C) slightly darker than the outside of lenticels color.

BRANCHES

Size: Mature branches and current season shoots are considered medium to large for the variety.

Diameter: Average as compared to other peach varieties. The current season shoots have a diameter from 6.0 to 8.0 millimeters, and mature branches have a diameter from 11.0 to 13.0 millimeters.

Surface texture: Average, wood which is several years old has no furrowed appearance.

Crotch angles: Primary branches are considered variable, but the crotch angles are generally between 45 degrees and 50 degrees from the horizontal axis. This particular characteristic is not considered distinctive of the variety, however.

Current season shoots:

Internode length: Generally between 25.0 and 32.0 millimeters.

Color of mature branches: Medium brown (RHS Grey Brown 199 A).

Current seasons shoots:

*Color*.—The color of new shoot tips is considered a pale yellow-green (RHS Yellow Green 145 A to RHS Yellow Green 145 B) on lower part of new shoot tips, whereas the upper part is darker and colored in brown-purple to red purple (RHS Greyed Purple 187 A to RHS Greyed Purple 187 B).

Spur:

*Spur length*.—Approximately 2.0 millimeters.

*Vegetative bud size*.—Length between 19.0 and 21.0 millimeters and width between 9.0 and 11.0 millimeters.

*Vegetative bud shape of apex*.—Rounded.

*Position of vegetative bud in relation to one year old shoot*.—Slightly held out.

LEAVES

Size: Considered medium for the species. The ratio leaf length/leaf width is 3.85.

Leaf length: Approximately 156.0 to 181.0 millimeters with leaf petiole. The medium length is 169.2 millimeters.

Leaf width: Approximately 37.0 to 51.0 millimeters. The medium width is 44.0 millimeters.

Leaf base shape: Concave.

Leaf form: Lanceolate.

Leaf tip form: Short, pointed and acuminate.

*Leaf blade incision of margin*.—Crenate.

Leaf color:

*Upper leaf surface*.—Green (RHS Green 137 A).

*Lower surface*.—A lighter green (RHS Yellow Green 146 A to RHS Yellow Green 146 B) than the upper leaf surface color.

Leaf texture: Smooth and glabrous.

Leaf venation: Pinnately veined.

Mid-vein:

*Color*.—Light green, almost yellow (RHS Yellow Green 145 D). The color may evolve with maturity.

Leaf margins: Slightly undulating.

Form: Considered slightly dentate.

Uniformity: Leaves are isolated or grouped by 2 or 3. In this last case, one leaf of normal size is found with one or two smaller leaves (at least 50% smaller).

Leaf petioles:

*Size*.—Considered medium.

*Length*.—About 12.0 to about 14.0 millimeters.

*Diameter*.—About 1.5 to 2.0 millimeters.

Petioles color:

*Upper petiole surface*.—Light green (RHS Yellow Green 144 A to RHS Yellow Green 144 B).

*Lower surface*.—Light green (RHS Yellow Green 145 A).

Leaf glands:

*Position of leaf glands (nectaries) on leaf*.—Predominantly on the upper part of the petiole.

*Size*.—Considered medium. Their length is about 2.0 millimeters and their width is about 1.0 millimeter.

*Number*.—Generally 2 or 3 glands per leaf.

*Type*.—Reniform.

*Color*.—On young leaves, leaf glands color is considered a light green (RHS Yellow Green 145 B). On older leaves, leaf glands color turns to a dark brown (RHS Grey Brown 199 A to RHS Grey Brown 199 B).

*Margins*.—Smooth and regular.

Leaf stipules:

*Generally*.—No leaf stipules were observed. But as seen in the characteristic relative to the leaves uniformity, it is possible to find leaves by groups of 2 or 3, with a normal-size leaf and smaller ones.

FLOWERS

Flower buds:

*Generally*.—At pre-floral stage of development, the floral buds are conic in form with a round tip. Their form is evolving until blooming, with variables dimensions. Just before blooming, floral buds are approximately between 7.0 and 9.0 millimeters wide and approximately 14.0 to 17.0 millimeters long.

*Color*.—This characteristic is dependent upon the proximity to bloom. At pre-floral stage of development (stage A), the bottom of the flowers buds, formed by the sepals, is of purple-brown color (RHS Greyed Purple 183 A to RHS Greyed Purple 183 B to RHS Greyed Purple 183 C or RHS Greyed Purple 187 B and RHS Grey Brown Group 199A at the base). The corolla, formed by the petals, is generally of dark pink color (RHS Red Purple 73 B to RHS Red Purple 73 C). Petals color shows an evolution until the end of flowering.

Hardiness: The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

Date of bloom: The blooming time generally begins during February and especially at the beginning of the month. However, the first bloom was observed on Feb. 28, 2012.

Blooming time: Considered very early to early-season in relative comparison to other commercial peach cultivars grown in the Pyrénées-Orientales departement, France. The date of full bloom is observed at the middle of the blooming period. The date of bloom varies slightly with climatic conditions and cultural practices. Thus the first full bloom was observed on February 28$^{th}$ until Mar. 5, 2012, then from February 7$^{th}$ until Feb. 20, 2013, then from February 9$^{th}$ until Feb. 19, 2014 and then from February 24$^{th}$ until Mar. 6, 2015.

Duration of bloom: Approximately 6 to 14 days. This characteristic varies slightly with the prevailing climatic conditions.

Flower type: The variety is considered to have a non-showy type flower (campanulate type).

Flower size: Considered small. Flower diameter at full bloom is approximately 15.0 to 18.0 millimeters.

Bloom quantity: Considered medium, approximately between 25 and 30 flowers per meter, with a good distribution and a high rate of fruit set.

Flower bud frequency: Generally 2 flower buds appear per node, occasionally 1.

Petal size:

*Generally*.—Considered small.

Length: Generally between 10.0 and 11.0 millimeters.

Width: Generally between 8.0 and 9.0 millimeters.

Petal form: Round-shaped.

Petal count: Generally 5.

Petal texture: Smooth, soft and glabrous.

Petal color: Both surfaces of the petal are colored with a dark pink color (RHS Red Purple 73 B to RHS Red Purple 73 C).

*Flower arrangement of petals*.—Overlapping.

Fragrance: Sweet.

Petal claw:

*Form*.—The claw is considered to have a triangular form, narrower at the base.

*Length*.—Approximately 2.0 millimeters.

*Width*.—Approximately 1.0 millimeter at the base.

*Color*.—RHS red Purple 63 A

Petal margins: Generally considered slightly undulating.

Petal apex:

*Generally*.—The petal apices are generally round and curved-shaped.

Flower pedicel:

*Length*.—Considered medium and having an average length of approximately 2.0 to 3.0 millimeters.

*Diameter*.—Considered average, approximately 1.5 millimeters.

*Color*.—Green (RHS Yellow Green N 144 A to RHS Yellow Green N 144 B).

Calyx:

*Internal surface texture*.—Smooth and glabrous.

*Color*.—At the stage F of blooming, when the flower is open, the inner surface of the calyx is matt and considered golden-orange (RHS Greyed Red 178 C to RHS Greyed Red 178 B). The outer surface of the calyx is considered of purple-brown color (RHS Greyed Purple 183 A to RHS Greyed Purple 183 B to RHS Greyed Purple 183 C or RHS Greyed Purple 187 B and RHS Yellow Green 144 A to RHS Yellow Green 144 B at the base).

Sepals:

*Number*.—Generally five sepals.

*Surface texture*.—The outer surface has a short, fine pubescent texture.

*Size*.—Average.

*Length*.—Approximately 5.0 millimeters.

*Width*.—Approximately 4.5 millimeters.

*Color*.—At the stage F of blooming, the outer surface of the sepals is considered of purple-brown color (RHS Greyed Purple 183 A to RHS Greyed Purple 183 B to RHS Greyed Purple 183 C or RHS Greyed Purple 187 B and RHS Yellow Green 144 A to RHS Yellow Green 144 B at the base). The inner surface of the sepals is matt and considered golden-orange (RHS Greyed Red 178 C to RHS Greyed Red 178 B).

Average number of stamens per flower: Approximately 36 to 44 stamens per flower.

Anthers:

*Anther position relative to petals*.—Shorter or equal.

*Generally*.—Medium in length.

*Color*.—Orange yellow color (RHS Yellow Orange 16 A to RHS Yellow Orange B) or red to red orange color (RHS Red Group N34 A or RHS Greyed Red Group 178 A). The color may evolve with maturity to turn in a red orange color.

Pollen production: Pollen is abundant, and has an orange yellow color (Approximately RHS Yellow Orange 17 B to RHS Yellow Orange 17 C) which may evolve with maturity. The present variety is considered auto-fertile (self-pollinating).

Filaments:

*Size*.—Medium length, between 8.0 and 12.0 millimeters in length. Filaments length is generally equal or higher to the pistil's length.

Color: Considered white (RHS White N 155 D) or light pink (approximately RHS Red Purple 62 C to RHS Red Purple D). The color becomes darker during the blooming.

Pistil:

*Number*.—Usually 1.

*Generally*.—Average in size.

*Length*.—Approximately 14.0 to 16.0 millimeters including the ovary. Generally equal to stamen length, if not slightly smaller.

*Color*.—Considered a very pale green (RHS Yellow Green Group 151 D) at the beginning of flowering, it becomes lighter and lighter (RHS Yellow Green 150 D) during the blooming and sometimes very slightly pinky (RHS Red Group 36D) at the end of the blooming.

*Surface texture*.—Glabrous.

FRUIT

Maturity when described: Very firm in ripe conditions (shipping ripe).

Date of first picking: Jun. 26, 2012.

Date of last picking: The date of harvest varies slightly with the prevailing climatic conditions. The 'CRISPONDA' variety has an early date of picking, and a grouped maturity. The maturity is grouped within 6 to 11 days and the harvest is generally performed in two runs. Last known picking times carry on from June 26$^{th}$ to Jul. 1, 2012, then from June 20$^{th}$ until Jun. 30, 2013 then from June 9$^{th}$ until Jun. 17, 2014 and then from June 20$^{th}$ until Jun. 27, 2015.

Size:

*Generally*.—Homogeneous in size, mainly A-2A.

Average cheek diameter: Approximately 63.0 to 70.0 millimeters.

Average axial diameter: Approximately 58.0 to 63.0 millimeters.

Typical weight: Generally about 135.0 to 175.0 grams. This characteristic is high dependent upon the prevailing cultural practices, and therefore is not particularly distinctive of the variety.

Fruit form:

*Generally*.—Round to slightly flattened. The fruit is generally uniform in symmetry, viewed from the suture's plane.

Fruit suture: Wide-mouthed and slightly marked, extending from the base to the apex. No apparent callousing or stitching exists along the suture line. Not pointed.

Suture:

*Color*.—The suture has generally a similar color to the whole fruit color, a luminous purple red (RHS Greyed Purple 187 A).

*Depth of fruit suture*.—The suture is not or slightly marked.

Ventral surface:

*Form*.—Smooth.

Apex: Non-prominent, generally slightly depressed.

Base: Semi-flared, shallow.

Stem cavity: Average depth of the stem cavity is about 12.0 to 16.0 millimeters. Average width is about 22.0 to 28.0 millimeters.

Fruit skin:

*Thickness*.—Considered very thick and strong, and the adherence of skin to flesh is strong to medium, depending on the fruit maturity.

*Texture*.—Glabrous, with a short pubescence.

*Lenticels*.—Absent.

*Taste*.—Aromatic, with a high level of sugars but semi-sweet due to acidity level between 6 and 9 meq/100 mL, which shows practically no variation after picking.

*Tendency to crack*.—None observed.

Color:

*Blush color*.—This blush color is a luminous and homogenous purple red (RHS Greyed Purple 187 A). The red blush covers 75% to 80% of the fruit skin surface on an orange red background (RHS Orange Red N34 A). The percentage of the blush on the fruit skin surface can vary, and is generally dependant upon the prevailing conditions under which the fruit was grown.

*Ground color*.—The ground color covers approximately 20 to 25% of the fruit skin surface, and is considered orange red (RHS Orange Red N 34 A).

Fruit stem: Medium in length, approximately 8.0 to 10.0 millimeters.

Diameter: Approximately 4.0 millimeters.

Color: Pale green (RHS Yellow Green 145 A).

Flesh:

*Ripens*.—Very homogenously, slowly. The flesh has a long shelf life.

*Texture*.—Very firm, very dense, juicy at harvest maturity stage, with crunchy texture when biting, but the flesh disintegrates quickly in the mouth.

*Fibers*.—Not fibrous.

*Aroma*.—Pronounced.

*Eating quality*.—Considered very good and aromatic.

*Flavor*.—Considered semi-sweet and very aromatic. The Brix is generally superior to 10 and acidity comprised between 6 and 9 meq/100 ml.

*Juice*.—Very juicy at complete maturity.

*Brix*.—Generally 10.0 to 14.0 degrees. This characteristic varies slightly with the number of fruit per tree; prevailing cultural practices; and the surrounding climatic conditions.

*Flesh color*.—Orange yellow flesh (RHS Yellow Orange 14 B to RHS Yellow Orange 14 C) usually with a pink red pigmentation near the pistil cavity.

STONE

Type: Clingstone, more or less adherent depending on the fruit maturity.

Size: Considered small for the variety. The stone size varies significantly depending upon the tree vigor, crop load and prevailing growing conditions.

Length: Approximately 25.0 to 27.0 millimeters.

Width: Approximately 22.0 to 24.0 millimeters.

Diameter: Approximately 18.0 to 20.0 millimeters.

Form: Elliptic to round.

Base: Straight.

Apex:

*Shape*.—The stone apex is short, pointed.

Stone cavity: Considered small in size, with an ovate-form and dimensions corresponding to the stone's dimensions.

Stone surface:

*Surface texture*.—The pit is transversely furrowed on its entire surface. Furrows are more pronounced toward the apex. The stone is pitted toward the base. Relief is prominent generally and present basally.

*Ridges*.—The surface texture is generally characterized by more prominent ridges along the ventral edges and is more prominent at the apical tip.

Ventral edge:

*Width*.—Considered small to medium, and having a dimension of approximately 1.5 to 2.0 millimeters at mid-suture.

Dorsal edge:

*Shape*.—Grooved.

Stone color: The color of the dry stone is generally considered light orange brown (RHS Greyed Orange 164 A to RHS Greyed Orange 164 B).

Tendency to split: Splitting is very low or absent, depending on climatic conditions between blooming period and stone hardening.

Kernel:

*Size*.—The kernel is considered medium to small.

*Length*.—Approximately 13.0 to 14.0 millimeters.

*Width*.—Approximately 9.0 to 11.0 millimeters.

*Thickness*.—Approximately 4.0 to 6.0millimeters.

*Form*.—Considered oblate and elliptic to round.

*Pellicle*.—The pellicle of the kernel has a short pubescence.

*Color*.—The kernel skin is a orange-brown (RHS Greyed Orange N167 B). The almond, which is the seed of the kernel, is white (RHS White 155 D) and has a bitter tasting. The kernel and its embryo are mature at the time of fruit maturity.

Use: The subject variety 'CRISPONDA' is considered to be a peach tree of the early season of maturity, suited for low chill areas and which produces fruits that are considered firm, attractively colored with a very luminous purple red. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long distance shipping.

Keeping quality: Remarkable. Fruit have a slow maturation and a long shelf life both on the tree after growth completion and after harvesting without alteration. After growth completion, fruits are preserved more than one week. After harvest, fruits are well preserved more than 4 weeks at 2.0 degree Celsius.

Shipping quality: Considered very good. The fruit of the new yellow peach variety showed minimal bruising of the flesh or skin damage after being subjected to normal harvesting and packing procedures. Its resistance to handling during harvest and packing and its long shelf life without alteration after harvest easily permit 3 to 4 weeks-shipping at 2 degrees Celsius.

Resistance to insects and disease: No particular susceptibilities were noted. The present variety is not very sensitive to powdery mildew, or conservation diseases and decay due to its thick and strong skin.

Although the new variety of peach tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

I claim:

1. A new and distinct variety of yellow peach tree as illustrated and described, characterized by fruits with high eating quality and very long shelf life without alteration before and after harvesting, with a semi-sweet orange yellow flesh, with a pink red pigmentation near the pistil cavity, and an attractive luminous skin with a high percentage of purple red blush on skin surface. This variety is suited for low chill areas.

* * * * *